US006628983B1

(12) United States Patent
Gagnon (10) Patent No.: US 6,628,983 B1
(45) Date of Patent: Sep. 30, 2003

(54) NUCLEAR IMAGING SYSTEMS AND METHODS WITH FEATURE-ENHANCED TRANSMISSION IMAGING

(75) Inventor: Daniel Gagnon, Twinsburg, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 186 days.

(21) Appl. No.: 09/696,153

(22) Filed: Oct. 25, 2000

(51) Int. Cl.[7] .................................................. A61B 6/00

(52) U.S. Cl. ...................................................... 600/431

(58) Field of Search .............................. 600/407, 425, 600/431, 436; 250/363.01, 363.02, 363.03, 363.04, 363.05, 363.1; 378/4, 21

(56) References Cited

U.S. PATENT DOCUMENTS

| | | | | |
|---|---|---|---|---|
| 3,848,130 A | | 11/1974 | Macovski | 250/369 |
| 4,878,186 A | | 10/1989 | Gagnon | 364/574 |
| 5,170,439 A | * | 12/1992 | Zeng et al. | 378/901 |
| 5,276,615 A | * | 1/1994 | Tournier Edmond et al. | 250/363.02 |
| 5,376,795 A | * | 12/1994 | Hasegawa et al. | 250/363.04 |
| 5,600,145 A | | 2/1997 | Plummer | 250/363.04 |
| 5,638,817 A | * | 6/1997 | Morgan et al. | 250/363.1 |
| 5,998,792 A | * | 12/1999 | DiFilippo | 250/363.03 |
| 6,175,118 B1 | * | 1/2001 | Takayama et al. | 250/363.07 |
| 6,205,347 B1 | * | 3/2001 | Morgan et al. | 600/407 |
| 6,384,416 B1 | * | 5/2002 | Turkington et al. | 250/363.03 |

FOREIGN PATENT DOCUMENTS

| | | |
|---|---|---|
| EP | 0 358 965 | 3/1990 |
| EP | 0 385 505 | 9/1990 |

OTHER PUBLICATIONS

"Introduction to Holospectral Imaging in Nuclear Medicine for Scatter Subtraction", Gagon, et al., IEEE Transactions on Medical Imaging, vol. 8, No. 3, Sep. 1989, pp245–250.
Pixies Advertising Literature (7 pages), Nov. 28, 1999–Feb. 1, 2000.

* cited by examiner

Primary Examiner—Sang Paik
(74) Attorney, Agent, or Firm—Fay, Sharpe, Fagan, Minnich & McKee, LLP (57) ABSTRACT

A transmission radiation source (30a) radiates at a plurality of energy levels within a specified energy range. The energy range is divided into two or more energy subranges. Detectors (20a–20c) detect the position or trajectory and energy of transmitted radiation and emitted radiation. A sorter (48) sorts the detected radiation into the appropriate energy subrange. Data for each subrange is stored in a plurality of transmission data memories (50a–50n). Reconstruction processors (52a–52n) generate a transmission image representation (54a–54n) representative of each energy subrange. A combine processor (60) weights each energy subrange image representation with an assigned weighting factor (64a–64n) to provide enhancement of at least one feature when the images are combined to generate weighted image representations (72, 74, 76). The plurality of transmission images are also combined with equal weighting to generate an image representation (70) used to generate attenuation correction factors (80) for correcting the emission data (46). A reconstruction processor (84) generates a corrected emission image representation (86). The emission image can be combined with one of the feature-enhanced structural images (72, 74, 76) using a combiner (92) and displayed, allowing the functional emission image to be located with respect to structural or anatomical features. Also, a feature-enhanced structural image (72, 74, 76), can advantageously be used to register the emission image (86) with an image (100) from another modality, such as a computed tomography (CT) image.

18 Claims, 6 Drawing Sheets

NUCLEAR IMAGING SYSTEMS AND METHODS WITH FEATURE-ENHANCED TRANSMISSION IMAGING

BACKGROUND OF THE INVENTION

The present invention relates generally to the art of nuclear medicine. It finds particular application to nuclear imaging techniques and apparatuses employing emission and transmission tomography. Although the present invention is illustrated and described herein primarily in reference to positron emission tomography (PET) and single photon emission computed tomography (SPECT), it will be appreciated that the present invention is also amenable to other noninvasive investigation techniques and other diagnostic modes in which a subject or patient is examined with transmitted radiation.

Diagnostic nuclear imaging is used to study a radionuclide distribution in a subject. Typically, one or more radiopharmaceuticals or radioisotopes are injected into a subject. The radiopharmaceuticals are commonly injected into the subject's blood stream for imaging the circulatory system or for imaging specific organs which absorb the injected radiopharmaceuticals. Gamma or scintillation camera detector heads are placed adjacent to a surface of the subject to monitor and record emitted radiation. For SPECT imaging, collimators are typically placed on the detector heads. For PET imaging, a coincidence detector detects concurrent receipt of a radiation event on two oppositely disposed heads. Often, the detector heads are rotated or indexed around the subject to monitor the emitted radiation from a plurality of directions. The monitored radiation data from the multiplicity of directions is reconstructed into a three-dimensional image representation of the radiopharmaceutical distribution within the subject. Such images typically provide functional and metabolic information.

Positron emission tomography (PET) is a branch of nuclear medicine in which a positron-emitting radiopharmaceutical such as $^{18}$F-fluorodeoxyglucose (FDG) is introduced into the body of a subject. Each emitted positron reacts with an electron in what is known as an annihilation event, thereby generating a pair of 511 keV gamma rays. The gamma rays are emitted in directions approximately 180° apart, i.e., in opposite directions.

A pair of detectors registers the position and energy of the respective gamma rays, thereby providing information as to the position of the annihilation event and hence the positron source. Because the gamma rays travel in opposite directions, the positron annihilation is said to have occurred along a line of coincidence connecting the detected gamma rays. A number of such events are collected and used to reconstruct a clinically useful image.

The energy spectrum for clinical positron annihilation imaging is typically characterized by a photopeak at 511 keV. Similarly, Compton scattered radiation contributes to counts having energies ranging as high as the Compton edge. In coincidence imaging, a dual energy window detection scheme is sometimes used. A window around the photopeak and a window in the vicinity of the Compton region are identified. A coincidence event is counted if both detectors detect temporally simultaneous events within the photopeak window, or if one detector observes an event in the photopeak window while the other simultaneously detects an event in the Compton window. In each case, a memory location is incremented to note the event and its location such that the respective events are weighted equally. Events in which both detectors observe Compton events are discarded.

Single photon emission computed tomography (SPECT) is another nuclear imaging technique used to study the radionuclide distribution in subjects. Typically, one or more radiopharmaceuticals are injected into a subject. The radiopharmaceuticals are commonly injected into the subject's blood stream for imaging the circulatory system or for imaging specific organs which absorb the injected radiopharmaceuticals. Gamma or scintillation camera heads are placed closely adjacent to a surface of the subject to monitor and record emitted radiation. In SPECT imaging, the detector head or heads are rotated or indexed around the subject to monitor the emitted radiation from a plurality of directions. The monitored radiation emission data from the multiplicity of directions is reconstructed into a three-dimensional image representation of the radiopharmaceutical distribution within the subject.

One of the problems with nuclear imaging techniques such as PET and SPECT is that photon absorption and scatter by portions of the subject between the emitting radionuclide and the camera head(s) distort the resultant image. One solution for compensating for photon attenuation is to assume uniform photon attenuation throughout the subject. That is, the subject is assumed to be completely homogenous in terms of radiation attenuation, with no distinction made for bone, soft tissue, lung, etc. This enables attenuation estimates to be made based on the surface contour of the subject. However, human subjects do not cause uniform radiation attenuation, especially in the chest.

In order to obtain more accurate radiation attenuation measurements, a direct measurement is made using transmission computed tomography techniques. In this technique, radiation is projected from a radiation source through the subject. Radiation that is not attenuated is received by detectors at the opposite side. The source and detectors are rotated to collect transmission data concurrently or sequentially with the emission data through a multiplicity of angles. This transmission data is reconstructed into a transmission image representation using conventional tomography algorithms. The radiation attenuation properties of the subject from the transmission image representation are used to correct for radiation attenuation in the emission data.

It is desirable to precisely locate the emission images relative to other anatomical details. In so doing, the diagnostic accuracy of the nuclear medicine image is increased. This is particularly so in the area of oncology, in which precise localization of nuclear medicine images aids in surgical and/or radiotherapeutic planning and for assessment of lesion progression and treatment effectiveness.

While transmission data has largely been successful in determining attenuation correction factors for the correction of the emission image data, the transmission image data itself has generally been of less than ideal resolution. The coarseness of the images could create uncertainties when localizing the emission image with respect to anatomical features.

One method of localizing the functional information is to merge the emission image representation with an image representation generated with another imaging modality that provides anatomical or structural details, such as x-ray computed tomography (CT), magnetic resonance (MR), or ultrasound image representations. When fusing images of different modalities, image registration of the two images is required to correct for any differences in geometric relations between the two images. Any misalignment of the two images impairs the diagnostic value of the fused images.

Image registration can be performed by a number of techniques, such as using discrete extrinsic or intrinsic landmarks known to bear a constant relationship to the subject's anatomy during the two studies, and using three-dimensional surface identification algorithms to construct numerical models of the external surface of the images. Such techniques allow the images to be aligned and oriented with respect to each other by translating, rotating, and descaling one or both of the image representations to allow the images to be superimposed or fused. However, given the lack of structural detail in nuclear medicine emission images and the low resolution of typical transmission images, significant uncertainties can remain when combining a nuclear medicine image with an image from a different modality. Moreover, inconvenience, cost, and multiple scans are generally required when obtaining scans from multiple modalities.

Imaging devices which combine a CT-like device with a gamma camera are known in the art. Such a device can reduce scan times by using correlated acquisition of nuclear medicine image data and CT image data. However, such a combined device is a less than optimal solution to the problem of nuclear medicine image localization due to cost and for logistical reasons. Also, although different modalities are combined on a single machine, this type of device retains the conventional approach of addressing separately the need for attenuation correction and the need for precise nuclear medicine image localization.

Transmission image quality can also be increased through increasing the number of counts, i.e., by increasing the source activity, increasing the imaging time, or both. Increasing the source activity, however, has the disadvantage of increasing cost and shielding requirements. Increasing the imaging time is generally undesirable for patient handling reasons. Also, both increasing source activity and increasing imaging time undesirably increase the dose of radiation received by the subject.

Accordingly, the present invention contemplates a new and improved nuclear medicine imaging method and apparatus which overcome the above-referenced problems and others.

SUMMARY OF THE INVENTION

In accordance with a first aspect of the present invention, a method of generating an image comprises providing a transmission radiation source emitting gamma rays at a plurality of energy levels and directing the emitted gamma rays through a subject to be imaged, the subject attenuating the transmission of the gamma rays and defining an energy range encompassing the emission energy levels. The energy range is divided into a plurality of energy subranges and gamma rays passing through the subject and falling within the defined energy range are detected. Detector head positions or trajectories and energies of the detected gamma rays are determined and this information is logged into a plurality of image data subsets based on the determined energy of the detected gamma rays, wherein each image data subset corresponds to one of the energy subranges. The steps of detecting, determining, and logging are repeated for a plurality of transmitted rays. The image data subsets are compared to determine one or both of: (1) variations in attenuation between different tissue types of the subject as a function of energy, and (2) variations in attenuation within each tissue type of the subject as a function of energy. Based on the determined attenuation variations, a weighting factor is assigned to each of the image data subsets and the image data subsets are combined in accordance with their assigned weighting factors to produce a weighted image data set, the weighting factors being assigned so as to enhance at least one structural feature in the weighted image data set. A feature-enhanced transmission image representation representative of the weighted image data set is then generated.

According to another aspect, a method of diagnostic imaging comprises transmitting radiation with a defined energy spectrum through a subject and converting the transmission radiation which has traversed the subject into electronic transmission data indicative of transmission radiation detector head position or trajectory and energy. In accordance with the energy data, the transmission trajectory data is sorted into a plurality of energy windows and the transmission trajectory data in each window is reconstructed into a corresponding electronic transmission image representation. The electronic transmission image representations are each weighted and the weighted transmission image representations are combined.

In yet a further aspect, the present invention provides a gamma camera comprising a transmission radiation source for generating radiation im a selected energy range and a detector for detecting emission radiation emitted from within a subject and transmission radiation from the transmission radiation source which has traversed a subject to be imaged, the subject attenuating the radiation, the detector generating position or trajectory and energy data. The gamma camera further comprises energy discrimination circuitry connected with the detector, the energy discrimination circuitry sorting detected transmission radiation in accordance with a plurality of energy subranges within the selected energy range; an electronic storage medium connected with the energy discrimination circuitry, the electronic storage medium storing a plurality of transmission data subsets, the data subsets comprising data grouped by energy in accordance with the plurality of energy subranges; at least one reconstruction processor connected with the electronic storage medium which generates a transmission image representation for each of the plurality data subsets; and a combine processor connected with the reconstruction processor which weights the transmission image representations and combines the plurality of weighted image representations to produce at least one weighted image representation, the weighting being selected to enhance at least one selected feature in each weighted image representation.

One advantage of the present invention is that it provides a transmission image providing increased anatomic structural detail without increasing imaging time or increasing radiation source activity.

Another advantage is that the transmission image data is maintained in a proper format for attenuation correction of the emission image data.

Another advantage of the present invention is that it provides enhanced transmission image data for improved registration of an emission image representation with an image representation of a different modality.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figures 1, 1A:
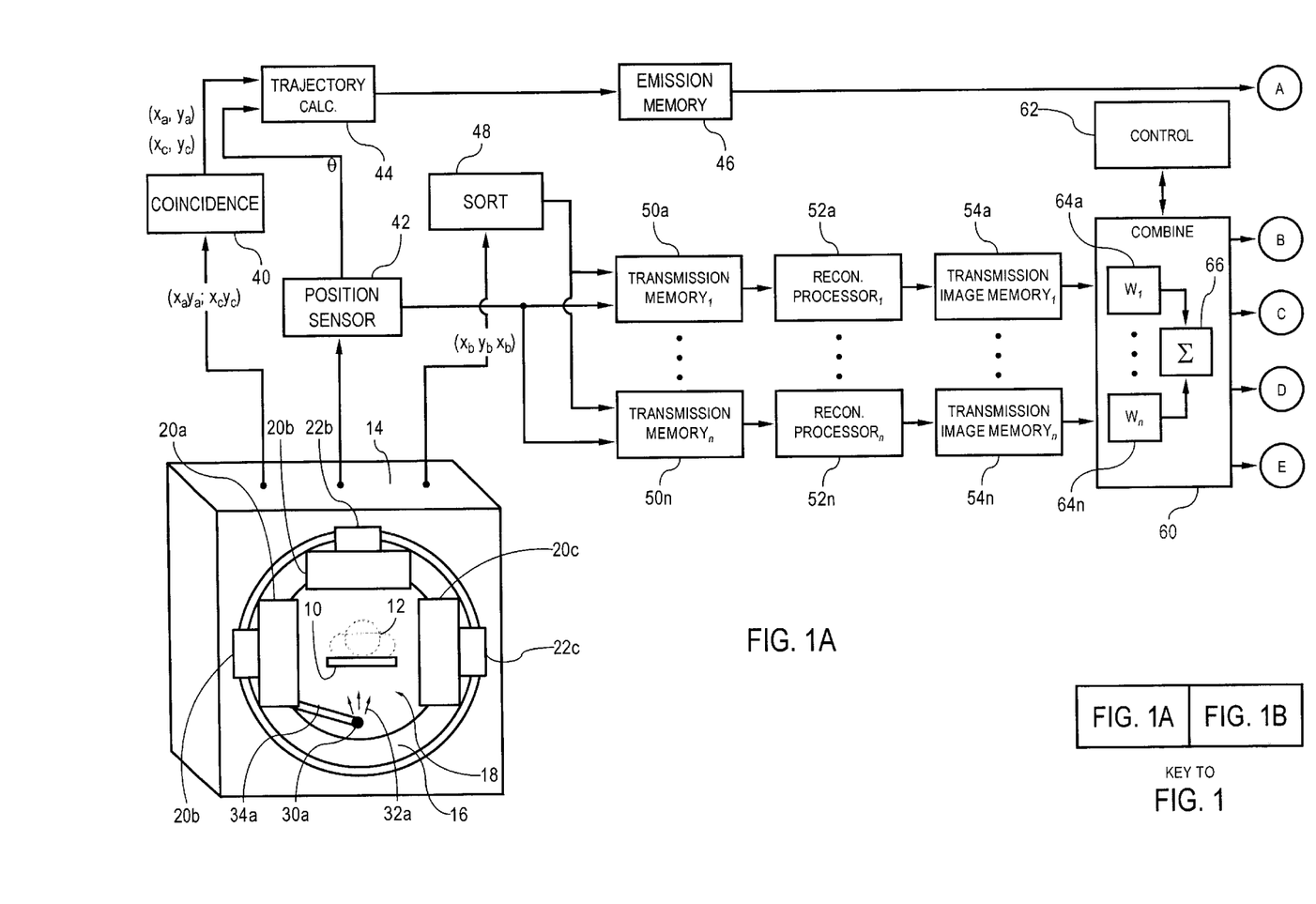
FIGS. 1A and 1B, taken together as FIG. 1, are a diagrammatic illustration of a first embodiment of a gamma camera in accordance with the present invention.
Figure 1B:
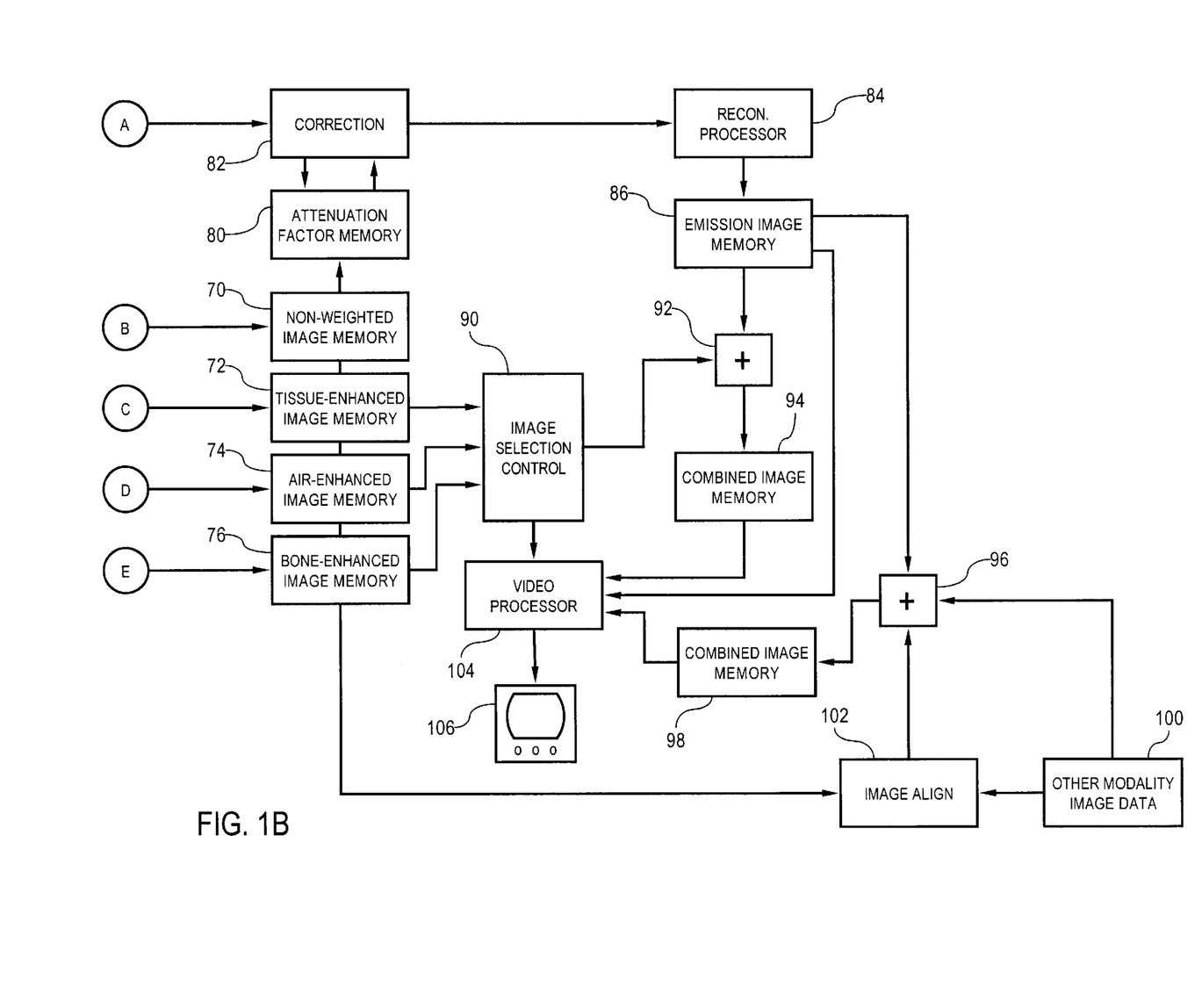
Figure 2A:
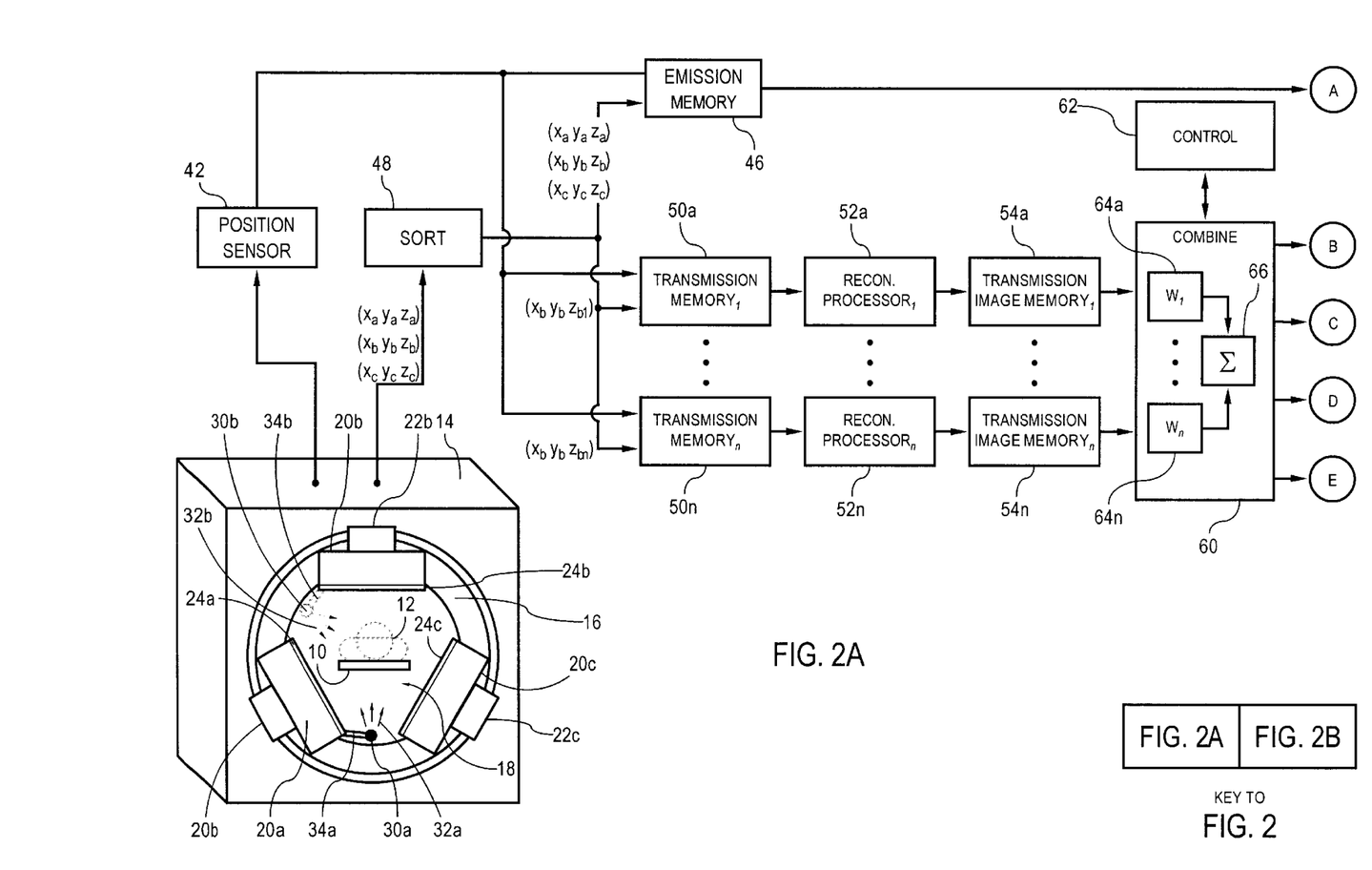
FIGS. 2A and 2B, taken together as FIG. 2, are a diagrammatic illustration of a second embodiment of a gamma camera in accordance with the present invention.
Figure 2B:
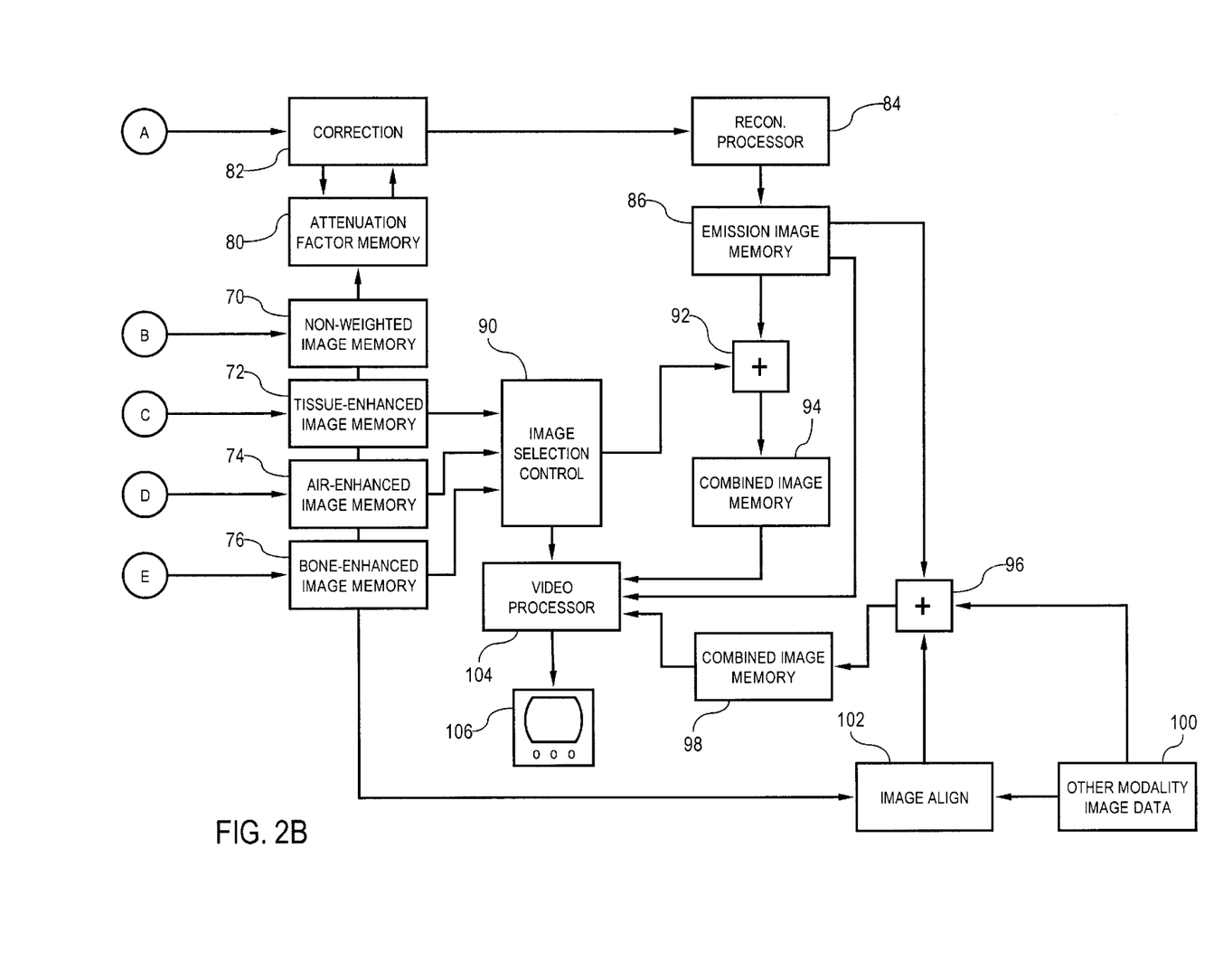

With reference to FIGS. 1 and 2, a diagnostic imaging apparatus includes a subject support 10, such as a table or couch, which supports a subject 12 being examined and/or imaged. The embodiments illustrated in FIGS. 1 and 2 can be, but are not necessarily, implemented in a gamma camera system capable of imaging in both PET and SPECT modes. Alternatively, the embodiments of FIGS. 1 and 2 can be implemented in dedicated PET and SPECT gamma camera systems, respectively. The subject 12 is injected with one or more radiopharmaceuticals or radioisotopes such that emission radiation is emitted therefrom optionally, the subject support 10 is selectively height adjustable so as to center the subject 12 at a desired height, e.g., so that the volume of interest is centered. A first or stationary gantry 14 rotatably supports a rotating gantry 16. The rotating gantry 16 defines a subject receiving aperture 18. In certain embodiments embodiment, the first gantry 14 is moved longitudinally along the subject support 10 so as to selectively position regions of interest of the subject 12 within the subject receiving aperture 18. Alternatively, the subject support 10 is advanced and retracted to achieve the desired positioning of the subject 12 within the subject receiving aperture 18.

Detector heads 20a, 20b, and 20c are individually positionable on the rotating gantry 16. The detector heads 20a–20c also rotate as a group about the subject receiving aperture 18, and the subject 12 when received, with the rotation of the rotating gantry 16. The detector heads 20a–20c are radially, circumferentially, and laterally adjustable to vary their distance from the subject and spacing on the rotating gantry 16. Separate translation devices 22a, 22b, and 22c, such as motors and drive assemblies, independently translate the detector heads radially, circumferentially, and laterally in directions tangential to the subject receiving aperture 18 along linear tracks or other appropriate guides.

Each of the detector heads 20a–20c has a radiation receiving face facing the subject receiving aperture 18. Each head includes a scintillation crystal, such as a large doped sodium iodide crystal, that emits a flash of light or photons in response to incident radiation. An array of photomultiplier tubes receives the light flashes and converts them into electrical signals x,y,z. A resolver circuit resolves the x, y-coordinates of each flash of light and the energy of the incident radiation. That is to say, radiation strikes the scintillation crystal causing the scintillation crystal to scintillate, i.e., emit light photons in response to the radiation. The photons are received by the photomultiplier tubes and the relative outputs of the photomultiplier tubes are processed and corrected to generate an output signal indicative of (i) a position coordinate on the detector head at which each radiation event is received, and (ii) an energy of each event. The energy is used to differentiate between various types of radiation such as multiple emission radiation sources, stray and secondary emission radiation, scattered radiation, transmission radiation, and to eliminate noise. In SPECT imaging, a projection image representation is defined by the radiation data received at each coordinate on the detector head. In PET imaging, the detector head outputs are monitored for coincident radiation events on two or more heads. From the position and orientation of the heads and the location on the faces at which the coincident radiation is received, a ray between the peak detection points is calculated. This ray defines a line along which the radiation event occurred. The radiation data from a multiplicity of angular orientations of the heads is then reconstructed into a volumetric image representation of the region of interest.

For SPECT imaging, the detector heads 20a–20c include mechanical collimators 24a, 24b, and 24c (FIG. 2), respectively, removably mounted on the radiation receiving faces of the detector heads 20a–20c. The collimators include an array or grid of lead vanes which restrict the detector heads 20a–20c from receiving radiation not traveling along selected rays in accordance with the selected imaging procedure. In this manner, each detector head at each angular position creates a projection image along rays defined by the collimator. For PET imaging, a SPECT camera without collimators on the detector heads can be employed.

In specific reference to FIG. 1, a nuclear medicine imaging apparatus is shown in a configuration for PET imaging in accordance with the present invention. In the embodiment shown, two of the detector heads, e.g., 20a and 20c, are arranged on the rotating gantry 16 on opposite sides of the receiving aperture 18 in facing relation. The receiving faces of the detectors 20a and 20c are advantageously aligned in generally parallel planes for receiving the coincidence emission counts. A transmission radiation source 30a is mounted to the first detector head 20a or the rotating gantry 16 and is collimated such that transmission radiation from the radiation source 30a is directed toward and received by the detector head 20b positioned across the subject receiving aperture from the radiation source 30a. In this manner, two detector heads, e.g., 20a and 20c are used for detecting emission radiation and the third head, e.g., 20b is used for detecting transmission radiation.

It will be recognized that the configuration illustrated in FIG. 1 is illustrative and exemplary only and many additional configurations are contemplated. For example, the present invention may be adapted to a two-head gamma camera system, e.g., wherein the detector head 20b is absent, or a three-head detector head systems wherein one of the three detector heads, e.g., the detector head 20b, is not used. In such cases, one (or more) transmission radiation sources are positioned so pass through the subject receiving aperture 18 to be received by an opposing detector head also receiving the emission radiation, with the emission and transmission radiation being distinguished based on their respective energies. Likewise, gamma camera systems including four or more detector heads are also contemplated.

Annihilation radiation events are identified by a coincidence detector 40 which identifies simultaneous scintillations in both heads and passes the x,y coordinates on each head and the angular orientation of each head from a position sensor 42 to a ray processor 44. Noncoincident and piled-up events are discarded. A ray processor identifies the trajectory or ray corresponding to each coincident event from the x,y coordinates of the scintillations on each head and the position of the heads which is stored in an emission memory 46. Transmission radiation from the transmission radiation source 30a are sorted by a sorter 48 on the basis of relative energies $z_b$ and stored in a plurality of transmission memories 50a–50n. Each of the memories corresponds to a preselected energy range or band.

In specific reference now to FIG. 2, a three-head embodiment, in a configuration suitable for SPECT imaging, is illustrated. The apparatus includes the first detector head 20a, the second detector head 20b, and the third detector head 20c arranged on the rotating gantry 16 spaced from one another around the subject receiving aperture 18. A radiation source 30a is mounted to the first detector head 20a such that transmission radiation 32a therefrom is directed toward and received by the second detector head 20b. The radiation source 30a is preferably collimated at the source. An optional second radiation source 30b can be optionally mounted on another detector head, e.g., the detector head 20b, in like manner such that transmission radiation therefrom can be directed toward and received by the opposing detector head, e.g., the detector head 20c. Likewise, it is to be appreciated that in still further embodiments, radiation sources can also be mounted to all three detector heads. In still further embodiments, systems having fewer than three detector heads, e.g., one- or two-head systems, are contemplated. Likewise, gamma camera systems including four or more detector heads are also contemplated. Single photon emission events and transmission radiation from the transmission radiation source 30a are sorted by a sorter 48 on the basis of relative energies and stored in an emission memory 46 and a plurality of transmission memories 50a–50n, respectively.

Referring again to FIGS. 1 and 2, the radiation source 30a preferably contains a radioactive line source, preferably a radionuclide held in a shielded steel cylinder 32a which is sealed at the ends. In this configuration, the radioactive source generates a radiation fan beam which passes through the subject receiving aperture. The radiation source can be stepped or rotated around the examination volume with the detector heads to obtain coverage of the volume of interest. The steel cylinder can be adjustably mounted onto the corresponding detector head through a pivoting arm mechanism 34a for retraction when the transmission source is in use. Alternatively, the radiation source 30a is a bar source, point source, flat rectangular source, disk source, or flood source.

The radiation source 30a emits gamma radiation across a relatively large energy range. In preferred embodiments, a single radioisotope emitting a plurality of specific energy bands is used, although the use of a plurality of radioisotopes emitting at different energy levels is also contemplated. In a particularly preferred embodiment, the transmission source 30a uses $^{133}$barium as the radioactive material. Barium-133 emits gamma radiation mainly at 356 keV, but also at 383 keV and 303 keV, thereby providing a relatively large useful energy band.

An angular position sensor 42, which may be, for example, optical, mechanical, or optomechanical, senses or indexes the position of the rotatable gantry 16 and radial, tangential, and circumferential shifts of the heads, and thus the positions of the detector heads 20a–20c in space, as it rotates about the subject receiving aperture 18 during data acquisition. The head positions recorded are used for transforming the recorded emission and transmission data into a subject coordinate.

The sorter or energy discrimination circuitry 48 first sorts the acquired emission data (FIG. 2) from the transmission data on the basis of the relative energies of the detected emission events. Second, the sorter sorts the transmission data into energy segments (FIGS. 1 and 2).

The position of detected events having an energy associated with emission events, for example 511 keV for positron annihilation in PET imaging, or characteristic emission energies of the particular radiopharmaceutical used for SPECT imaging, are stored in the emission data memory 46.

As stated above, the transmission radiation source 30a employed in accordance with this teaching provides a relatively large usable energy band. The transmission energy spectrum is divided into n contiguous energy bands or windows covering the transmission energy spectrum, wherein n is at least two, and is preferably from two to about eight. Detected transmission events are sorted according to the designated energy windows and stored in a corresponding one of n transmission memories 50a–50n. For example, in a preferred embodiment, $^{133}$Ba is used as the transmission radiation source, which emits at 303 keV, 356 keV, and 383 keV. Accordingly, the emission spectrum from about 300 keV to about 400 keV is sampled and segmented into a plurality of contiguous energy windows, preferably 3, each centered about one of the peaks.

Transmission radiation data is preferably collected first such that the emission data can be processed into a corrected image as it is collected. However, it is to be appreciated that the emission and transmission acquisition portions of the imaging operation need not be performed in a set order. In addition, emission and transmission radiation data may be acquired simultaneously.

Each of the transmission data memories 50a–50n corresponding to the plurality of defined energy windows, is connected to an associated one of n reconstruction processors 52a–52n, each of which is in turn connected to an associated one of n transmission image memories 54a–54n. Alternately, a single reconstruction processor can reconstruct all of the energy windows on a time shared basis. The reconstruction processors 52a–52n reconstruct the transmission data stored in the transmission data memories 50a–50n to generate n transmission image representations which are stored in the transmission image memories 54a–54n. The reconstruction process can change according to the mode of collection, the nature of the study, and the types of collimators used (i.e., fan, cone, parallel beam, and/or other modes). Each of the transmission image representations contained in memories 54a–54n are then combined using an image combining processor or circuitry 60. Control circuitry 62 determines weighting factors or functions 64a–64n, one for each of the transmission image representations contained in memories 54a–54n. The weighting factors 64a–64n are determined in accordance with selected features or tissue types to be enhanced in the resultant weighted image representation. A summing circuit 66 combines some or all of the image representations 54a–54n in accordance with the determined weighting factors or functions 64a–64n.

A non- or equally-weighted combined transmission image representation is generated, e.g., wherein each of the transmission image representations in the memories 54a–54n is summed or averaged with equal weighting, and stored in a combined image memory 70. This equally weighted transmission image representation is used to determine attenuation correction factors which are stored in an attenuation factor memory 80. An emission data correction processor 82 corrects each emission data in accordance with the attenuation factors. For example, for each ray along which emission data is received, an emission correction processor 82 calculates a corresponding ray through the transmission attenuation factors stored in the memory 80. Each ray of the emission data is then weighted or corrected by the emission data correction processor 82 inversely with the attenuation factors. The corrected emission data are reconstructed by an emission radiation reconstruction processor 84 to generate a three-dimensional emission image representation that is stored in a volumetric emission image memory 86. Alternately, the transmission data correction is performed as a part of the reconstruction process. A video processor 104 withdraws selected portions of the data from the image memory 86 to generate corresponding human-readable displays on a video monitor 106. Typical displays include reprojections, selected slices or planes, surface renderings, and the like.

In addition to generating an equally weighted sum or average of the n transmission image representations contained in the memories 54a–54n, one or more feature-enhanced image representations are also generated by varying the weighting factors or functions accordingly. The weighting factors or functions 64a–64n are determined in accordance with (1) the attenuation characteristics of each of the three tissue types generally present in the imaged volume (i.e., bone, soft tissue, and air (lung)) which vary as a function of the energy of the transmission source material, and (2) the attenuation differences for each tissue type, e.g., bone and soft tissue, as a function of the energy of the transmission source material. By examining the differences between the plurality of transmission image representations corresponding to the plurality of energy windows, weighting factors or functions can be determined that allow the n transmission image representations to be combined so as to enhance certain structural features in the resultant image. Accordingly, the plurality of transmission image data sets stored in memories 54a–54n are statistically analyzed and weighting factors are determined that emphasize a selected tissue type.

One or more feature-enhanced image representations, such as soft-tissue-enhanced, bone-enhanced, and/or air enhanced image representations, are generated and stored in memories 72, 74, and/or 76, respectively. In certain embodiments, a tissue-enhanced image representation is generated. In other embodiments, a bone-enhanced image representation is generated. In still other embodiments, an air-enhanced image representation showing aerated lung boundaries is generated. Optionally, the enhanced images can be used to correct the emission data. When a plurality of feature-enhanced image representations are generated, an image selection control 90 allows an operator to select one of the enhanced transmission image representations from the memories 72, 74, and 76 to be fused with the corrected emission image representation. A combining circuit or processor 92 produces a combined image representation showing the emission or functional image as well as anatomical or structural features from the selected feature-enhanced transmission image data. This allows features of the functional emission image, such as lesions, to be localized with respect to the subject's anatomy using structural features shown in the feature-enhanced transmission image. The fused image representation is stored in a memory 94. The video processor 104 withdraws selected portions of the data from the combined image memory 94 to generate corresponding human-readable displays on the video monitor 106. In certain embodiments, the image selection control 90 also allows the operator to select a feature-enhanced transmission image representation for display without being combined with the emission image, thereby providing CT-like functionality.

Figure 3:
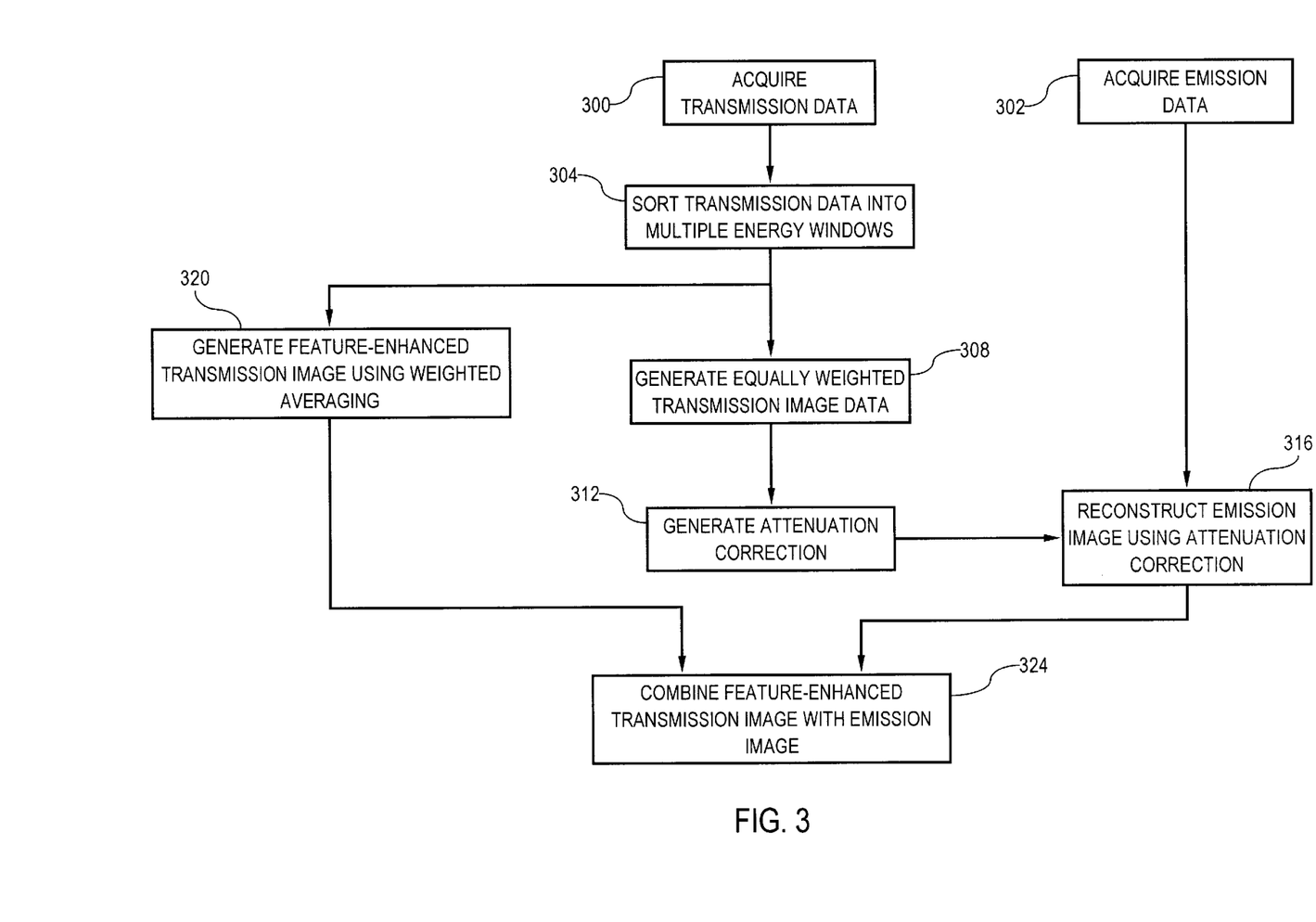
FIGS. 3 and 4 are flow charts outlining two exemplary methods of the present invention.

Referring now to FIG. 3, a flow chart outlining a method of the present invention wherein an emission image representation is combined with a feature-enhanced transmission image representation is illustrated. The method includes an initial acquisition of emission and transmission data (steps 300 and 302), as described above. The transmission data is sorted into n energy windows based on the energy of the recorded transmission events (step 304), wherein n is an integer of 2 or greater, preferably from 2 to about 8, most preferably 3. A non-weighted transmission image representation is generated (step 308) by reconstructing the transmission data from each energy window and taking a non-weighted sum or average of the resultant image representations. The non-weighted transmission image representation is used to generate attenuation correction factors for the emission image data (step 312). The emission image representation is reconstructed using the calculated attenuation correction factors (step 316). Weighted sums or averages of the reconstructed transmission image representations from the n energy windows are used to provide feature-enhanced transmission image representations (step 320), as detailed above. The reconstructed emission image representation and the feature-enhanced transmission image representation are then superimposed (step 324).

Referring again to FIGS. 1 and 2, an image registration processor 102 registers the emission image representation 86 with a digital image representation 100 acquired from another imaging modality, such as a CT, MR, or ultrasound image representation. In a preferred embodiment, the other modality image representation 100 is a CT image representation. Common structural features are detected in one of the enhanced transmission image representations saved in the memories 72, 74, or 76, and in the other modality image representation 100. The detected common features are then used to map or correlate the functional image representation 86 to the other modality image representation 100, e.g., by calculating appropriate rotation, translation, and scaling factors. Since structural or anatomical features such as air boundaries, soft-tissue features, and bone structure, are more accurately represented in the corresponding enhanced image representations, and the use of the enhanced transmission image representation in accordance with this teaching provide more accurate registration of the emission image representation with the other modality image representation. In preferred embodiments, the bone-enhanced image representation 76 is used to register the emission image representation 86 and the other modality image representation 100. After registration, a combiner 96 then fuses or superimposes the registered emission and other modality image representations, and the resultant fused image representation is stored in a memory 98. The video processor 104 withdraws selected portions of the data from the combined image memory 98 to generate corresponding human-readable displays on a video monitor 106.

Figure 4:
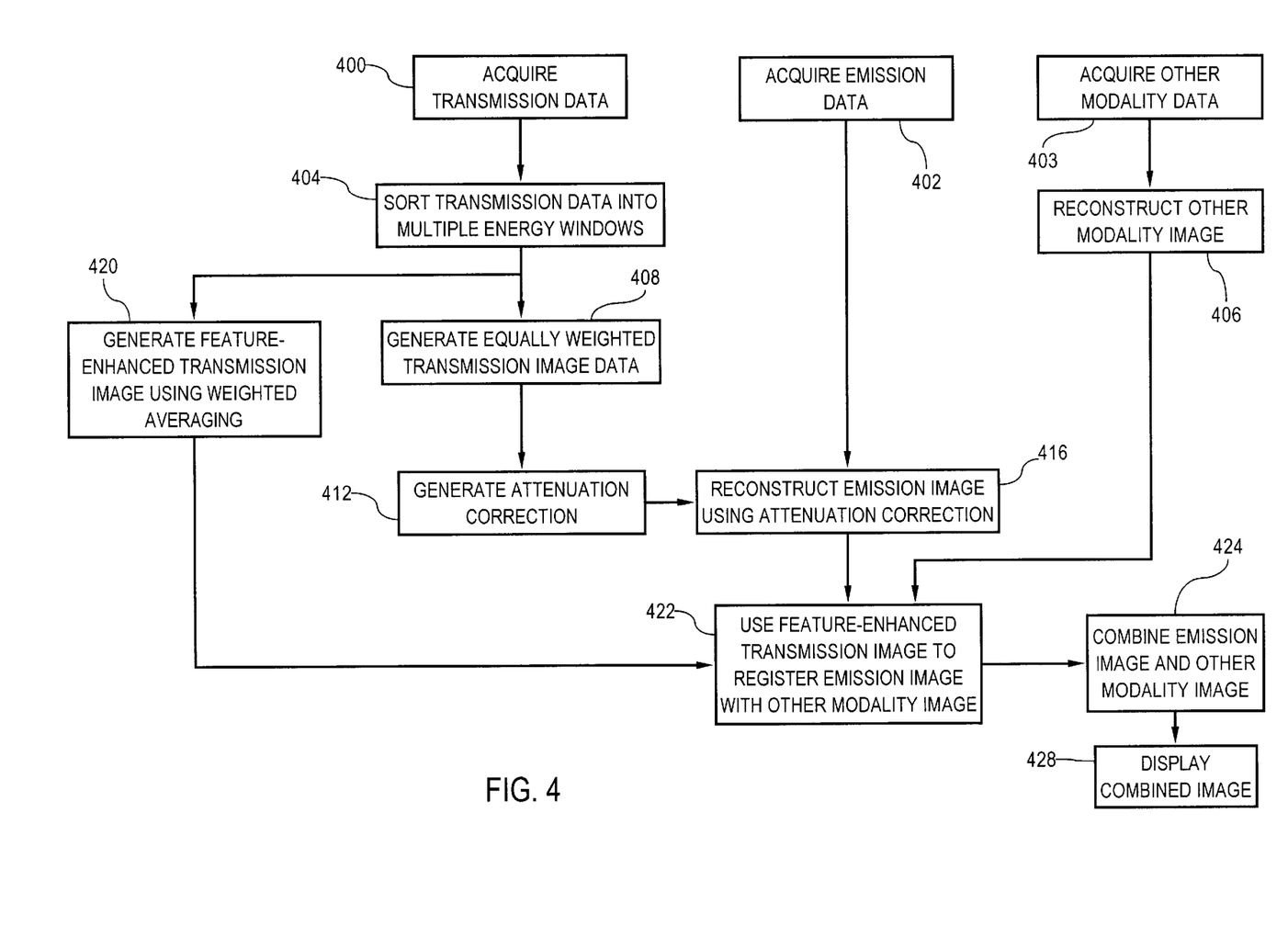

Referring now to FIG. 4, a flow chart is illustrated outlining a method of the present invention wherein an emission image representation is registered with an image representation from another imaging modality, using a feature-enhanced transmission image representation in accordance with this teaching to perform the registration. The method includes an initial acquisition of emission (step 402) and transmission data (step 400), as described above. Image data is acquired from another imaging modality (step 403) and reconstructed to form an image representation (step 406). The transmission data is sorted into n energy windows based on the energy of the recorded transmission events (step 404), wherein n is an integer of 2 or greater, preferably from 2 to about 8. A non-weighted transmission image representation is generated (step 408) by reconstructing the transmission data from each energy window and taking a non-weighted sum or average of the resultant image representations. The non-weighted transmission image representation is used to generate attenuation correction factors for the emission image data (step 412). The emission image representation is reconstructed using the calculated attenuation correction factors (step 416). Weighted sums or averages of the reconstructed transmission image representations from the n energy windows are used to provide a feature-enhanced transmission image representation (step 420), as detailed above. The feature-enhanced transmission image representation is used to register the emission image representation with the other modality image representation (step 422). The other modality image representation and the emission image representation are then superimposed (step 424). The fused image is then output to a display (step 428).

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A method of generating an image, comprising:

providing a transmission radiation source emitting gamma rays at a plurality of energy levels and directing the emitted gamma rays through a subject to be imaged, the subject attenuating the transmission of the gamma rays;

defining an energy range encompassing the emission energy levels;

dividing the energy range into a plurality of energy subranges;

detecting the gamma rays passing through the subject and falling within the defined energy range;

determining positions and energies of the detected gamma rays;

logging the determined position and energy information into a plurality of image data subsets based on the determined energy of the detected gamma rays, each image data subset corresponding to one of the energy subranges;

repeating the steps of detecting, determining, and logging for a plurality of transmitted rays;

comparing the image data subsets to determine one or both of: (1) variations in attenuation between different tissue types of the subject as a function of energy, and (2) variations in attenuation within each tissue type of the subject as a function of energy;

based on the determined attenuation variations, assigning a weighting factor to each of the image data subsets and adding the image data subsets together in accordance with their assigned weighting factors to produce a weighted image data set, the weighting factors being assigned so as to enhance at least one structural feature in the weighted image data set; and generating an feature-enhanced transmission image representation representative of the weighted image data set.

2. The method according to claim 1, wherein the transmission radiation source is barium-133, wherein the defined energy range ranges from about 300 keV to about 400 keV, and wherein the number of energy subranges is from 2 to 8.

3. The method according to claim 1, wherein the enhanced structural feature is selected from the group consisting of bone, soft tissue, and aerated lung tissue.

4. The method according to claim 1, further including:

administering to the subject a gamma radiation-emitting radionuclide composition which emits gamma radiation having a characteristic energy level;

detecting single photon emissions from the radionuclide composition within the subject to generate emission image data;

combining the plurality of transmission image data subsets to generate an attenuation map of the subject;

reconstructing an emission image representation from the emission image data;

during the reconstructing, using the transmission image data to compensate for attenuation; and combining the emission image representation with the feature-enhanced transmission image representation to generate a superimposed image representation.

5. A method of generating an image, comprising:

providing a transmission radiation source which transmits rays of radiation at a plurality of energy levels within a range through a subject to be imaged;

dividing the range into a plurality of subranges;

detecting the rays of radiation passing through the subject and falling within the range;

determining positions and energies of the detected rays;

logging the determined position and energy information into a plurality of transmission image data subsets based on the determined energy of the detected rays, each transmission image data subset corresponding to one of the energy subranges;

assigning a weighting factor to each of the transmission image data subsets and combining them together in accordance with their assigned weighting factors to produce a weighted transmission image data set, the weighting factors being assigned so as to emphasize at least one tissue type in the weighted transmission image data set;

generating a feature-enhanced transmission image representation representative of the weighted transmission image data set;

administering to the subject a radiopharmaceutical composition generating emission radiation;

detecting the emission radiation to generate emission image data;

equally weighting the plurality of transmission image data subsets and combining them to generate an attenuation map of the subject;

correcting the emission image data using the attenuation map to generate corrected emission image data;

reconstructing an emission image representation from the corrected emission image data; and combining the emission image representation with the feature-enhanced transmission image representation to generate a superimposed image representation.

6. The method according to claim 1, further including:

administering to the subject a gamma radiation-emitting radionuclide composition which emits gamma radiation having a characteristic energy level;

detecting emissions from the radionuclide composition within the subject to generate emission image data;

combining the plurality of transmission image data subsets to generate an attenuation map of the subject;

reconstructing an emission image representation from the emission image data;

correcting one of the emission image data and the emission image representation using the attenuation map;

providing an image representation from another imaging modality, the other modality image representation being selected from an x-ray computed tomography image representation, a magnetic resonance image representation, and an ultrasound image representation, the other modality image representation being at least partially coextensive with the emission image representation;

identifying common structural features in the feature-enhanced transmission image representation and the other modality image representation;

correlating and aligning the corrected emission image representation and the other modality image representation based on the identified common structural features; and combining the emission image representation with the other modality image representation to generate a superimposed image representation.

7. The method according to claim 6, wherein the feature-enhanced transmission image representation is a bone-enhanced image representation.

8. A method of diagnostic imaging comprising:

transmitting radiation with a defined energy spectrum through a subject;

converting the transmission radiation which has traversed the subject into electronic transmission data indicative of transmission radiation trajectory and energy;

in accordance with the energy data, sorting the transmission trajectory data into a plurality of energy windows;

reconstructing the transmission trajectory data in each window into a corresponding electronic transmission image representation;

weighting each of the electronic transmission image representations; and adding the weighted transmission image representations together.

9. The method according to claim 8, further including:

injecting the subject with a radioisotope which emits radiation;

converting emission radiation emitted within the subject into electronic emission data indicative of emission radiation trajectory;

reconstructing the electronic emission trajectory data into an electronic emission image representation.

10. The method according to claim 9, further including:

correcting one of the electronic emission data and the electronic emission image representation with the weighted transmission representations.

11. The method according to claim 9, further including:

with another imaging modality, generating an electronic other modality image representation which clearly depicts a first aspect of the subject;

weighting the electronic transmission image representations to emphasize the first aspect and combining the weighted electronic transmission image representations to produce a combined weighted transmission image representation;

aligning the combined weighted transmission image representation and the other modality image representation; and combining the emission image representation and the other modality image representation.

12. A gamma camera comprising:

a transmission radiation source for generating radiation in a selected energy range;

a detector for detecting emission radiation emitted from within a subject and transmission radiation from the transmission radiation source which has traversed a subject to be imaged, the subject attenuating the radiation, the detector generating position and energy data;

energy discrimination circuitry connected with the detector, the energy discrimination circuitry sorting detected transmission radiation in accordance with a plurality of energy subranges within the selected energy range;

an electronic storage medium connected with the energy discrimination circuitry, the electronic storage medium storing a plurality of transmission data subsets, the data subsets comprising data grouped by energy in accordance with the plurality of energy subranges;

at least one reconstruction processor connected with the electronic storage medium which generates a transmission image representation for each of the plurality data subsets; and a combine processor connected with the reconstruction processor which weights the transmission image representations and adds the plurality of weighted image representations together to produce at least one weighted image representation, the weighting being selected to enhance at least one selected feature in each weighted image representation.

13. The gamma camera according to claim 12, further including a display system for converting the weighted image representation into a human-viewable image.

14. The gamma camera according to claim 12, wherein the transmission radiation source is barium-133, wherein the defined energy range ranges from about 300 keV to about 400 keV, and wherein the number of energy subranges is from 2 to 8.

15. The gamma camera according to claim 12, wherein the combine processor further compares the plurality of transmission image representations to determine one or both of (i) variations in attenuation between different tissue types of the subject as a function of energy and (ii) variations in attenuation within each tissue type of the subject as a function of energy, and assigns a weighting factor to each of the plurality of image representations based on the determined attenuation variations.

16. A gamma camera comprising:

a transmission radiation source for generating radiation in a selected energy range;

a detector for detecting emission radiation emitted from within a subject and transmission radiation from the transmission radiation source which has traversed the subject, the detector generating position and energy data;

energy discrimination means connected with the detector, the energy discrimination means sorting detected transmission radiation in accordance with a plurality of energy subranges within the selected energy range;

a storage device connected with the energy discrimination means, the storage device storing a plurality of transmission data subsets, the data subsets comprising data grouped by energy in accordance with the plurality of energy subranges;

a reconstruction processor connected with the storage device, said reconstruction processor generating a transmission image representation for each of the plurality data subsets;

a combination processor connected with the reconstruction processor, said combination processor weighting the transmission image representations and adding the plurality of weighted transmission image representations together to produce at least one weighted transmission image representation, the weighting being selected to emphasize at least one tissue type in each weighted transmission image representation; and an emission data correction processor for correcting the emission data using the weighted transmission image representation to generate corrected emission image data for reconstruction into an emission image representation with the image reconstruction processor.

17. The gamma camera according to claim 16, further including:

a memory for storing an image representation from another imaging modality, the other modality image representation being at least partially coextensive with the corrected emission image representation;

a registration processor for identifying common structural features in one of the weighted transmission image representations and the other modality image representation, and for correlating and aligning the corrected emission image representation and the other modality image representation based on the identified common structural features; and an image combiner for combining the emission image representation with the other modality image representation to generate a superimposed image representation.

18. The gamma camera according to claim 17, further including:

a video processor for formatting operator selected portions of the corrected emission image representation, the weighted image representations, and the superimposed image representation into a display format; and a monitor for converting the display format portions into an operator selected display.

* * * * *